United States Patent
Yates

Patent Number: 5,558,671
Date of Patent: Sep. 24, 1996

[54] IMPEDANCE FEEDBACK MONITOR FOR ELECTROSURGICAL INSTRUMENT

[76] Inventor: David C. Yates, 7534 Galway Ct., West Chester, Ohio 45069

[21] Appl. No.: 311,297

[22] Filed: Sep. 23, 1994

Related U.S. Application Data

[63] Continuation-in-part of Ser. No. 95,797, Jul. 22, 1993, Pat. No. 5,403,312.

[51] Int. Cl.$^6$ .................................................. A61B 17/36
[52] U.S. Cl. ........................ 606/38; 606/34; 606/42; 606/50
[58] Field of Search .................. 606/32–35, 37–42, 606/45–50

[56] References Cited

U.S. PATENT DOCUMENTS

| | | | |
|---|---|---|---|
| 2,031,682 | 2/1936 | Wappler et al. | |
| 4,126,137 | 11/1978 | Archibald | 606/38 |
| 4,171,700 | 10/1979 | Farin | 606/34 |
| 4,416,276 | 11/1983 | Newton et al. | 606/35 |
| 4,474,179 | 10/1984 | Koch | 606/38 |
| 4,494,539 | 1/1985 | Zenitani et al. | 606/34 |
| 4,608,981 | 9/1986 | Rothfuss et al. | |
| 4,633,874 | 1/1987 | Chow et al. | |
| 4,651,280 | 3/1987 | Chang et al. | |
| 4,655,216 | 4/1987 | Tischer | |
| 4,658,819 | 4/1987 | Harris et al. | 606/34 |
| 4,671,274 | 6/1987 | Sorochenko | |
| 4,685,459 | 8/1987 | Koch et al. | |
| 4,961,047 | 10/1990 | Carder | |
| 4,985,030 | 1/1991 | Melzer et al. | |
| 5,057,107 | 10/1991 | Parins et al. | |
| 5,085,659 | 2/1992 | Rydell | |
| 5,104,025 | 4/1992 | Main et al. | |
| 5,151,102 | 9/1992 | Kamiyama et al. | |
| 5,167,658 | 12/1992 | Ensslin | 606/34 |
| 5,190,517 | 3/1993 | Zieve et al. | |
| 5,201,900 | 4/1993 | Nardella | |
| 5,207,691 | 5/1993 | Nardella | |
| 5,300,070 | 4/1994 | Gentelia et al. | |
| 5,335,668 | 8/1994 | Nardella | |
| 5,342,357 | 8/1994 | Nardella | 606/40 |
| 5,389,098 | 2/1995 | Tsuruta et al. | |
| 5,417,687 | 5/1995 | Nardella et al. | |
| 5,423,809 | 6/1995 | Klicek | |
| 5,429,636 | 7/1995 | Shikhman et al. | |
| 5,437,662 | 8/1995 | Nardella | 606/39 |

FOREIGN PATENT DOCUMENTS

| | | |
|---|---|---|
| 0518230 | 12/1992 | European Pat. Off. |
| 0517244 | 12/1992 | European Pat. Off. |

(List continued on next page.)

OTHER PUBLICATIONS

Automatically Controlled Bipolar Electrocoagulation–"COA–COMP", Neurosurg. Ref. (1984) 187–190; B. Vallofors and B. Bergdahl.

Radio Frequency Energy and Impedance Feedback, SPIE vol. 1068 Catheter–Based Sensing and Imaging Technology (1989).

Instrument for Stomach Resection and Bowel Anastomosis Used During Closed Procedures, Department of Surgery of Mukachevo City Hospital, N. G. Vittenberger, Jan.–Feb. 1958, First Issue (the 211th).

*Primary Examiner*—Angela D. Sykes
*Assistant Examiner*—Michael Peffley

[57] ABSTRACT

An impedance monitoring device is provided for monitoring the electrical impedance of tissue as it is treated with electrosurgical energy. Based on a predicted model of tissue impedance and a number of initial impedance readings, the impedance at which tissue treatment is completed is predicted. More particularly, a minimum impedance level is measured and a function of the minimum impedance is used to determine impedance at which coagulation is completed. A control device is provided for bringing the output of the generator within an optimum range based on a system load curve. In one embodiment the impedance monitoring device is used in conjunction with a bipolar electrosurgical instrument. Preferably, the instrument comprises electrically opposite electrodes located on one or more tissue engaging surfaces for engaging tissue to be treated.

11 Claims, 10 Drawing Sheets

FOREIGN PATENT DOCUMENTS

| | | |
|---|---|---|
| 2573301 | 5/1986 | France . |
| 2455171 | 8/1976 | Germany . |
| 3942998A1 | 7/1991 | Germany . |
| 2213381 | 8/1989 | United Kingdom . |
| WO93/08754 | 5/1993 | WIPO . |
| WO93/13718 | 7/1993 | WIPO . |
| WO94/10925 | 5/1994 | WIPO . |
| WO94/24951 | 11/1994 | WIPO . |
| WO94/24949 | 11/1994 | WIPO . |
| 9424949 | 11/1994 | WIPO .................................. 606/34 |
| WO95/09576 | 4/1995 | WIPO . |

| SW | CC | T | D | S | RF |
|----|----|----|----|----|----|
| 0 | 0 | 0 | 0 | 0 | 1 |
| 1 | X | X | X | X | 0 |
| X | 1 | X | X | X | 0 |
| X | X | 1 | X | X | 0 |
| X | X | X | 1 | X | 0 |
| X | X | X | X | 1 | 0 |

0 = LOGIC 0
1 = LOGIC 1
X = DON'T CARE

SW = SWITCH (INVERTED) 128
CC = COAG. COMPLETE 125
T = TIMER 127
D = OPEN CIRCUIT 126
S = SHORT CIRCUIT 124

FIG. 12

IMPEDANCE FEEDBACK MONITOR FOR ELECTROSURGICAL INSTRUMENT

This is a continuation-in-part of U.S. application Ser. No. 08/095,797 filed on Jul. 22, 1993 now U.S. Pat. No. 5,403,312, incorporated herein by reference.

FIELD OF THE INVENTION

This invention relates to electrosurgical tissue treatment, and in particular, to a method and apparatus for controlling the electrosurgical treatment of tissue by measuring impedance of the tissue being treated by an electrosurgical device.

BACKGROUND OF THE INVENTION

Electrosurgical generators are used to deliver therapeutic electrical energy to surgical instruments. These instruments are used for example, for cutting, coagulation, tissue welding, ablation, and dissection. Both monopolar and bipolar generators typically supply electrosurgical energy in the radio frequency (RF) range to such instruments. Usually such generators include controls that regulate the voltage and/or current so that a select power level is approximately delivered and a maximum power level is not exceeded.

When such RF generators are used, the primary control is the experience of the surgeon who responds to what is observed to be happening to the tissue as it is treated with the RF energy. Often, particularly for endoscopic procedures, surgeons cannot readily see what is happening to the tissue. Also, the change in tissue properties due to the RF energy may occur so quickly so as not to afford time for the surgeon to react soon enough to turn off electrical energy to the instrument. As a result, some problems which may occur include tissue charring, sticking of tissue to the electrodes of the surgical instrument, and over or under treatment of tissue.

It has been recognized that the tissue impedance changes as RF energy is applied to the tissue. Attempts have been made to control the power delivered to the tissue as the tissue impedance changes. For example, current has been controlled based on the change in the voltage or the power delivered by the generator to tissue. The differential quotient of tissue impedance as RF power is applied to the tissue has been used to determine an initial power level and to switch off RF power when the differential quotient of impedance reaches a preset value.

Notwithstanding these control arrangements, there is a continuing need for improvement in the control of electrosurgical energy deliverance to the tissue and/or determination of when tissue treatment has reached an optimal level.

In particular there is a need to provide a device and method for determining the end point of coagulation for a variety or a range of tissue impedance, due to, e.g., varying tissue composition, tissue types and treated tissue areas and/or volumes.

SUMMARY OF THE INVENTION

The present invention provides an impedance monitoring device and/or method which monitors the impedance of tissue between poles of a therapeutic electrosurgical instrument. Based on a model of expected tissue impedance behavior over time with the deliverance of electrosurgical energy, the monitored tissue impedance is used to determine tissue status. This will be described in more detail below. A signal indicating status of tissue is provided either to a user or to an instrument controller. The device may also include a switch which automatically turns off the electrical energy when treatment is completed.

In accordance with the present invention, a tissue impedance monitor is provided which continuously measures tissue impedance as electrical energy is delivered to tissue. According to known tissue impedance models, tissue impedance initially drops as electrical energy is applied and then begins to rise again as coagulation occurs. The present invention provides for establishing a value for the minimum impedance, i.e., when the impedance is at its lowest value as the energy is applied. Then, the impedance value anticipated to provide the desired tissue effect is determined by calculating a selected function of the established minimum impedance. When the measured impedance rises to the level of the impedance value for the desired result, e.g., coagulation, tissue welding or a level of diathermy, the instrument will indicate or provide a response for such event. The present invention is preferably adapted so that the condition is detected for a range of expected tissue impedances which varies according to tissue type, area and/or volume.

In a preferred embodiment the desired tissue condition is where coagulation is completed. When this point has been reached a feedback signal is provided to a control unit or to the user, at which time the energy supply is switched off. The feedback signal may, for example, provide a visual, audible or tactile signal to a user, and/or may provide instructions to a control unit to automatically turn off energy supplied to the tissue.

Optionally, the device may also include a switch, adapted to turn off electrical energy when a short circuit condition is detected, when an open circuit condition is detected or when the device is on, i.e., supplying current or voltage for a preset maximum amount of time.

In accordance with one aspect of the present invention, an electrosurgical apparatus for coagulating tissue during a surgical procedure comprises an end effector with opposing interfacing surfaces which may be closed towards each other to engage tissue to be electrosurgically treated. Preferably the end effector includes first and second elements movable relative to one another for engaging tissue to be coagulated therebetween. At least one of the electrical poles of the instrument is comprised of an electrode associated with at least one of the first and second elements. The electrode is in contact with the tissue to be coagulated. A power controller responsive to a power control signal provides RF energy to the tissue contacting electrode(s) of the first and/or second elements.

Impedance measuring circuitry is coupled to the RF generator output and measures the impedance of the tissue between electrodes corresponding to the first and second poles. Feedback circuitry is coupled to the impedance measuring circuitry. The feedback circuitry includes a first device for determining a minimum impedance value and holding said minimum impedance value. A second device provides a threshold determining circuit coupled to the first device. The threshold determining circuit determines a threshold impedance value as a function of the held minimum impedance value.

The threshold determining circuit may comprise an analog device for determining the function of minimum impedance or a digital circuit including, for example, a look up table for determining the threshold impedance value based on an input minimum impedance value.

After a threshold value has been determined, a first comparator compares the measured impedance value to threshold impedance value and generates a power control signal to the power controller to control the RF energy delivered to the tissue upon the condition of the measured impedance value exceeding the threshold impedance value.

A power controller may include at least one electrical switch for selectively supplying RF energy to the instrument to coagulate tissue positioned between the first and second elements.

The power controller may selectively switch off the power supplied to the tissue under a number of conditions. The controller may be used to switch off power when the measured impedance value exceeds the threshold impedance value, when an open circuit condition or a short circuit condition exists, or if voltage and current is supplied for a period of time exceeding a maximum.

Another aspect of the present invention provides a control device for bringing the energy output of the generator within an optimal range determined by a system load curve. The control device uses measured load impedance to determine the desired energy level output and compares the desired energy output to the actual energy delivered to a target including tissue. The control device takes the resulting comparison and controls the generator output accordingly.

Although the instrument may be a monopolar device or a multipolar device including two or more than two poles, the end effector preferably includes two electrically opposite electrodes corresponding to two electrically opposite poles.

In the preferred bipolar device, electrically opposite electrodes of each of the poles are located on one or both of the opposing surfaces. Each of the first and second electrically opposite poles comprises at least one tissue contacting electrode. The electrodes are arranged on the distal end of the electrosurgical device so that when the first and second elements close together to engage tissue, opposite electrodes are located between a portion of the engaged tissue. The impedance monitoring circuit monitors the impedance of the tissue between the electrodes during the delivery of RF energy through that tissue. As described above a minimum impedance is measured from which threshold impedance is calculated. A comparator compares the measured impedance values to the determined threshold impedance value and generates a control signal to switch off the RF power delivered to the tissue, upon the condition of measured impedance value exceeding the threshold impedance value.

In one preferred embodiment each of the electrodes corresponding to the first pole are offset with respect to the interfacing surface from each of the electrodes corresponding to the second pole. In other words, the electrodes are offset from each other so that they are not diametrically opposed from each other on interfacing surfaces or they are separated and insulated from each other on the same surface.

In the preferred embodiment the electrosurgical instrument compresses tissue in a compression zone between the first interfacing surface and the second interfacing surface and applies electrical energy through the compression zone. More preferably, the compression zone is an area defined by a compression ridge on one of the interfacing surfaces which compresses the tissue against the other interfacing surface. Alternatively or in addition, there may be a compression ridge on both interfacing surfaces.

One embodiment includes a cutting element associated with an end effector. The cutting element is arranged to cut tissue at or near the coagulation site. Preferably, the coagulation is completed prior to any mechanical or other cutting at or around the coagulation site. Once tissue is coagulated or cauterized, the cutting element may be used to cut through the coagulated tissue or between two zones of tissue coagulation.

In another embodiment, the hemostatic device is incorporated into a linear cutter similar to a linear cutting mechanical stapler. In this embodiment the hemostatic device comprises two substantially parallel and elongated electrode bars which are associated with one pole, and a slot for cutting means to travel between the bars. Optionally one or more rows of staples may provide on each side of the slot and bars to provide additional hemostasis.

In operation, tissue is clamped between two jaws of the instrument, and electrical energy in the form of radio frequency ("RF") energy is supplied to the compressed tissue to coagulate or cauterize blood vessels along the two substantially parallel bars. Based on the impedance modeling of the device with this specific electrode configuration, an appropriate function of the minimum impedance is incorporated into the impedance feedback circuit to determine an appropriate threshold impedance level. A warning mechanism is used to warn the user when the impedance is out of range or exceeds the threshold impedance level. Also the warning signal may be directed to a control circuit or power controller adapted to then provide an appropriate instrument response, including where appropriate to turn off the RF energy delivered to the tissue.

In accordance with another aspect of the present invention a method of operating apparatus for electrosurgically treating tissue during surgical procedure is provided. Accordingly, a preferred method comprises the steps of: applying RF energy to tissue to be electrosurgically treated by means of an electrosurgical instrument; measuring the impedance of the tissue between electrodes corresponding to two poles of the electrosurgical instrument; generating the impedance signal representative of the impedance of the tissue; and controlling the RF energy applied to the electrosurgical instrument in response to the impedance signal.

The step of controlling the RF energy applied to the electrosurgical instrument may comprise the steps of: determining and holding minimum impedance value; determining a threshold impedance value based on a function of the minimum impedance value; comparing measured impedance values to the threshold impedance value; and generating a control signal to control or switch off the power of the controller upon the condition of measured impedance value exceeding the threshold impedance value.

In accordance with yet another aspect of the present invention, a method of operating an electrosurgical apparatus for coagulating tissue during surgical procedure comprises the steps of: providing an electrosurgical instrument having an end effector comprising the first and second tissue engaging surfaces, at least one of said first and second tissue engaging surfaces including thereon a tissue contacting electrode, associated with a first pole of an electrosurgical system and at least one of said first and second tissue engaging surfaces containing thereon a second tissue contacting electrode associated with a second pole of the system; engaging tissue to be coagulated between the first and second tissue engaging surfaces; selectively controlling RF energy supplied to the first and second tissue contacting electrodes for coagulating tissue positioned therebetween; measuring the impedance of the treated tissue; determining and holding a minimum impedance value; determining a threshold impedance value based on a function of the minimum impedance value; comparing measured impedance values to the threshold impedance value; and controlling or switching off the RF energy connected to the first and second electrodes upon the condition of the measured impedance value exceeding the threshold impedance value.

Other objects and advantages of the invention will apparent from the following description, the accompanying drawings and the following claims.

DETAILED DESCRIPTION OF THE INVENTION

While the present invention is generally applicable to a variety of electrosurgical instruments both monopolar and multipolar, and both conventional and endoscopic, it will be described herein with reference to a bipolar linear cutting instrument.

The primary purpose of the impedance monitoring device is to determine when the tissue has been treated to a desired degree. Preferably this treatment is completed when the tissue has been cauterized and before excessive tissue sticking, burning or charring occurs. The impedance of tissue as it is being heated with electrosurgical energy generally follows a characteristic tissue impedance curve. According to the impedance curve, generally the impedance will decrease, arrive at a minimum value, and then rise as coagulation and tissue desiccation occurs. At an impedance or within a range of impedances on a characteristic curve, coagulation will predictably occur.

Figure 12:
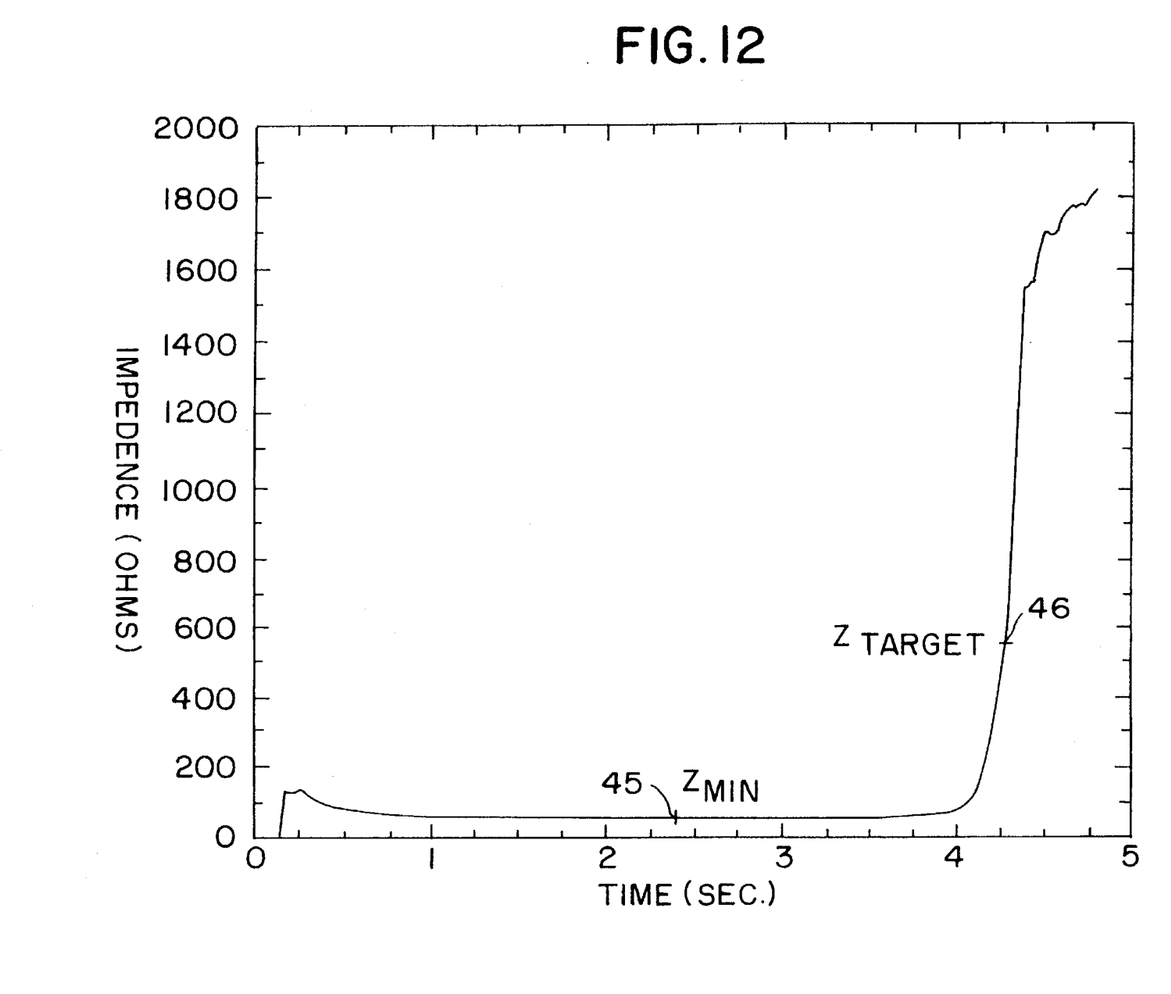
FIG 12 a characteristic curve illustrating the change in impedance over time during application of electrosurgical energy to tissue using the electrosurgical instrument illustrated in FIG. 1.

FIG. 12 is a characteristic impedance curve illustrating the change in tissue impedance over time, during the application of electrosurgical energy using the electrosurgical instrument illustrated in FIGS. 1–5. The present invention determines a threshold impedance on the curve at which coagulation has occurred, $Z_{target}$ 46. This impedance is based on the value of the lowest impedance on the curve, $Z_{min}$ 45, i.e., when the impedance has stopped falling and begins to rise. A function of the minimum impedance $f(Z_{min})$ is used to approximately predict a point at which coagulation occurs, $Z_{target}$ 46.

Figure 10:
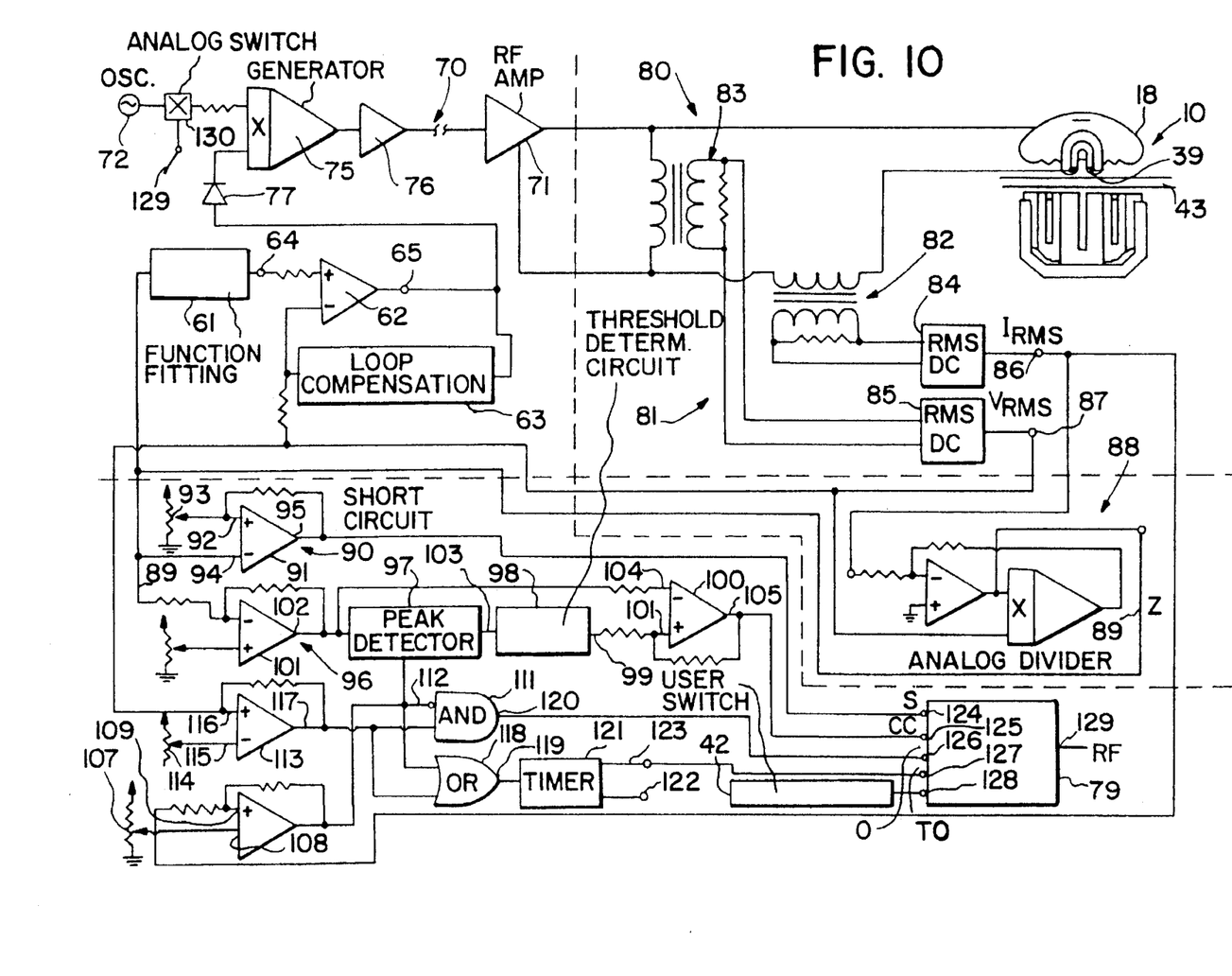
FIG. 10 is a schematic block diagram of an analog embodiment of the controller for use in the apparatus of FIG. 1.

Referring now to FIG. 10 there is illustrated a schematic block diagram of an analog embodiment of the impedance monitoring device of the present invention. The impedance monitoring device determines when coagulation is complete as well as other instrument parameters, for example, if there is an open circuit, short circuit or if voltage and current is supplied to the tissue for more than a predetermined maximum amount of time. Such conditions may indicate a problem with the instrument and/or tissue engaged by the instrument. For example, if excessive, not enough, or inappropriate tissue is engaged by the instrument.

The instrument 10 is positioned to engage tissue to be treated. Then, when appropriately positioned, RF energy is supplied to the tissue.

A generator 70 supplies RF energy to the tissue engaged by the end effector 15 of the instrument 10. Preferably, 30 to 200 volts RMS at a fundamental frequency, preferably of a sinusoidal waveform at a frequency of about 300 Khz to 3 Mhz is supplied with a current of about 0.1 to 4.0 amps. The generator 70 is turned on by a user operated switch 42. The user operated switch 42 provides a signal to the controller 79 to turn on the energy. The output 129 of the controller is coupled to an analog switch 130. When output 129 provides an "RF on"signal to the switch, 130, an oscillator 72, coupled to an analog multiplier 75 through the switch 130, supplies a voltage of a known frequency to the analog multiplier 75. The output of the analog multiplier 75 is coupled to a driver 76 which is coupled to the input of an RF amplifier 71. An amplified RF signal is supplied by the generator 70 to a circuit 80 which includes the first electrode 39 and second electrode (anvil 18) of the instrument 10, and the tissue 43 to be treated by the instrument 10.

The current and voltage delivered to the tissue is measured and an RMS current ("$I_{RMS}$") and an RMS voltage ("$V_{RMS}$") is determined.

A voltage and current sensor 81 senses the current and voltage delivered to the tissue. The voltage and current sensor 81 includes a low impedance current transformer 82 in series with the generator 70; and a high impedance voltage transformer 83 connected in parallel across the generator 70. Preferably the current transformer 82 has, for example, a 1:20 winding ratio and a 50 ohm resistor in parallel with the secondary of the transformer. Preferably the voltage transformer 83 has, for example, a 20:1 winding ratio and a 1K ohm resistor in parallel with the secondary of the transformer.

The output of the current transformer 82 is coupled to an RMS converter 84. The RMS converter 84 converts the sensed current to a DC signal to provide output 86, representative of $I_{RMS}$. The output of the voltage transformer 83 is coupled to an RMS converter 85. The RMS converter 85 converts the voltage signal into an DC signal and provide output 87, representative of $V_{RMS}$.

The measured impedance, Z, is then calculated from the measured $I_{RMS}$ and $V_{RMS}$. The outputs 87, 85 of $V_{RMS}$ and $I_{RMS}$ are supplied to an analog divider 88 which divides the $V_{RMS}$ by the current $I_{RMS}$ to provide an output signal 89 representative of the measured impedance, Z.

From the $I_{RMS}$, $V_{RMS}$ and measured impedance, Z, the impedance monitoring device determines whether a short circuit or open circuit condition exists, whether voltage and current has been delivered for an amount of time exceeding a predetermined maximum, and whether coagulation is complete.

A short circuit condition is determined by comparing the measured impedance, Z, to a predetermined short circuit impedance threshold at or below which short circuit is likely to exist ("$Z_{SC}$"). If the measured Z is at or below the $Z_{SC}$, a short circuit signal is provided to the controller.

The impedance signal 89 is input to a short circuit detector 90 comprised of a comparator. The positive input 92 of the comparator is connected to a potentiometer 93 which sets the threshold impedance, $Z_{SC}$. When the impedance signal 89 causes the input at the negative input 94 of the comparator 91 to be lower than that at the positive input 92, an "on" condition occurs at the output 95 of the comparator 91. This condition is communicated to a logic controller 79 which provides a preprogrammed instrument response, which, in this embodiment, includes turning off RF energy.

An open circuit condition exists if there is a voltage between the electrodes 18, 39, and no current. An open circuit is determined as follows: If the $V_{RMS}$ is above a predetermined minimum threshold indicating a voltage, $V_{thresh}$, and the $I_{RMS}$ is below a predetermined minimum current threshold indicating a current, $I_{thresh}$, then an open circuit signal is provided to a controller.

A current threshold detector 106 includes a potentiometer 107 coupled to the negative input 108. The potentiometer 107 sets the $I_{thresh}$ level so that when a current is present, the current detector 106 will indicate as such. The $I_{RMS}$ signal 86 is connected to the positive input 109 of the comparator 106. Thus, when the $I_{RMS}$ is greater than the value, $I_{thresh}$, set by the potentiometer 107, a positive voltage appears at the output 110 of the current threshold detector 106.

Similarly, a voltage threshold detector 113 includes a potentiometer 114 connected to the negative input 115. The potentiometer 114 sets the voltage threshold at which the threshold detector 113 registers a positive output, $V_{thresh}$ when a minimum voltage is present. The $V_{RMS}$ signal is input to the positive input 116 of the threshold detector 113. Thus, if the $V_{RMS}$ exceeds the $V_{thresh}$ set by the potentiometer 114, a positive voltage will appear at the output 117 of the voltage threshold detector 113.

The output 117 of the voltage threshold detector 113 is also coupled to an AND gate 111 and the output 110 of the current threshold detector 106 is coupled to an inverted input 112 of the AND gate 111. The AND gate 111 acts as an open circuit detector. When the $V_{RMS}$ exceeds the $V_{thresh}$ and where the $I_{RMS}$ does not exceed $I_{thresh}$, a logic 1 will appear at the output 120 of the AND gate 111 indicating an open circuit. The output 120 of the AND gate 111 is coupled to the controller 79 to communicate the open circuit status.

If current or voltage is supplied an extended period of time and a coagulation complete condition has not been detected, it may indicate, for example, that the instrument is not clamped on tissue or that a malfunction has occurred. If the $V_{RMS}$ is above the predetermined $V_{thresh}$ or the $I_{RMS}$ is above $I_{thresh}$, then a timer is turned on. If the timer is on for a period of time greater than a predetermined maximum amount of time, $T_{max}$, then a time over signal is provided to the controller. If the duration of the timer on is not greater than $T_{max}$ then the device continues to supply RF current to the tissue and continues to measure current, voltage and impedance, etc. as described above.

The output 110 of the current threshold detector 106 is coupled to an OR gate 118 which is coupled to a timer 121. If the $I_{RMS}$ exceeds the $I_{thresh}$, the output 110 of the current threshold detector 106 will present a logic 1 to the OR gate 118 which will then turn on the timer 121.

Similarly the output 117 of the voltage threshold detector 113 is coupled to the OR gate 118. If the $V_{thresh}$ is exceeded by $V_{RMS}$, the OR gate 118 will present a logic 1 at its output 119 and turn on the timer 121. The output 123 of the timer 121 is coupled to the controller 79. When the timer 121 has been activated for an amount of time that exceeds a preset threshold time, $T_{max}$, the output 123 will be a logic 1. The timer is reset with the user activated switch 42 which is coupled to the timer reset input 122, when the instrument 10 is reset.

A coagulation complete condition is determined as follows: First, $Z_{min}$ is determined. Then, a target impedance at which coagulation is complete, $Z_{target}$, is calculated as a function of the minimum impedance. The initial impedance, $Z_{min}$, $Z_{target}$, slope of the impedance curve, and time to complete may vary for a given application and/or instrument, but tend to correlate to a function of minimum impedance. Depending on the instrument used and/or the actual desired result, the actual function of minimum impedance may vary. In this particular embodiment $f(Z_{min})$ is linear: $f(Z_{min})=0.2Z+500$. This function is bound, i.e., where $Z_{min}$ is >560 ohms, then $Z_{target}$ is $Z_{min}+50$ ohms. $f(Z_{min})$ may be a different function. It may be continuous, non-continuous, linear, non-linear, a piecewise approximation and/or in the form of a look-up table. $f(Z_{min})$ may also be bound at different values.

The impedance signal 89 is used to determine tissue coagulation as follows: First, a determination is made whether the measured Z is a minimum impedance, $Z_{min}$. The impedance signal 89 is inverted and offset by a gain offset inverter 96. The output of the gain offset inverter 96 is in turn is coupled to a peak detector 97. The output 102 of the gain offset inverter is representative of an inverted and offset measured Z, i.e., $(-Z+k)$. $Z_{min}$ will now be the highest offset value of $(-Z+k)$ encountered.

The peak detector 97 thus detects and holds the highest value of the inverted and offset measured impedance, Z, which is $Z_{min}$. When $Z_{min}$ has occurred, the output 103 of the peak detector 97 is representative of $(-Z_{min}+k)$. RF energy is continued to be applied to the tissue and the monitoring for short circuit, open circuit and time over as well as looking for a $Z_{min}$ continues until a Z is equal to $Z_{target}$.

When the $Z_{min}$ has been determined, function of the $Z_{min}$, $(f(Z_{min}))$ is calculated to provide a impedance, $Z_{target}$, at which treatment (coagulation) is completed. The output 103 of the peak detector 97 is coupled to a threshold determining circuit 98 which calculates the function of $Z_{min}$ to determine the $Z_{target}$. The output 99 of the threshold determining circuit is representative of $Z_{target}$ when the measured impedance is equal to $Z_{min}$.

A continuous comparison is made between Z and $f(Z_{min})$. It should be noted here that $f(Z_{min})$ is continuously calculated as $f(Z)$ until a $Z_{min}$ is detected. The comparison is continuously made between Z and $f(Z)$ until $Z_{min}$ is determined. This does not have a significant consequence, however, because it is anticipated that $f(Z)$ will be larger than Z during tissue treatment and a premature coagulation complete signal therefore will not occur.

If measured Z is less than or equal to the $Z_{target}$ then RF energy is continued to be supplied and steps described above are carried out until a signal has been provided to the controller that there is an open circuit signal, short circuit signal, a time over signal, or a coagulate complete signal. If the measured Z is greater than or is equal to "$Z_{target}$," then a signal is provided to the controller that coagulation has been completed. Again it is noted that in this embodiment, Z has been inverted and shifted in order to accommodate $Z_{min}$ determination via the peak detector 97. The impedance values referred to in this paragraph are the actual impedance values The output 99, $Z_{target}$, of the threshold determining circuit 98 is coupled to the positive input 101 of a comparator OP amp 100. The output 102 of the gain offset inverter 96 is coupled to the negative input 104 of the comparator 100. The comparator 100 compares the −Z+k representative value which is input to the negative input 104 of the comparator 100, to the $Z_{target}$ representative value which is calculated as a function of $-Z_{min}+k$. If −Z+k is less than or equal to the $Z_{target}$, the comparator output 105 will be positive. That is, if the measured Z is greater than $f(Z_{min})$, a coagulation complete signal will appear at the output 105 of the comparator 100.

Figure 11:
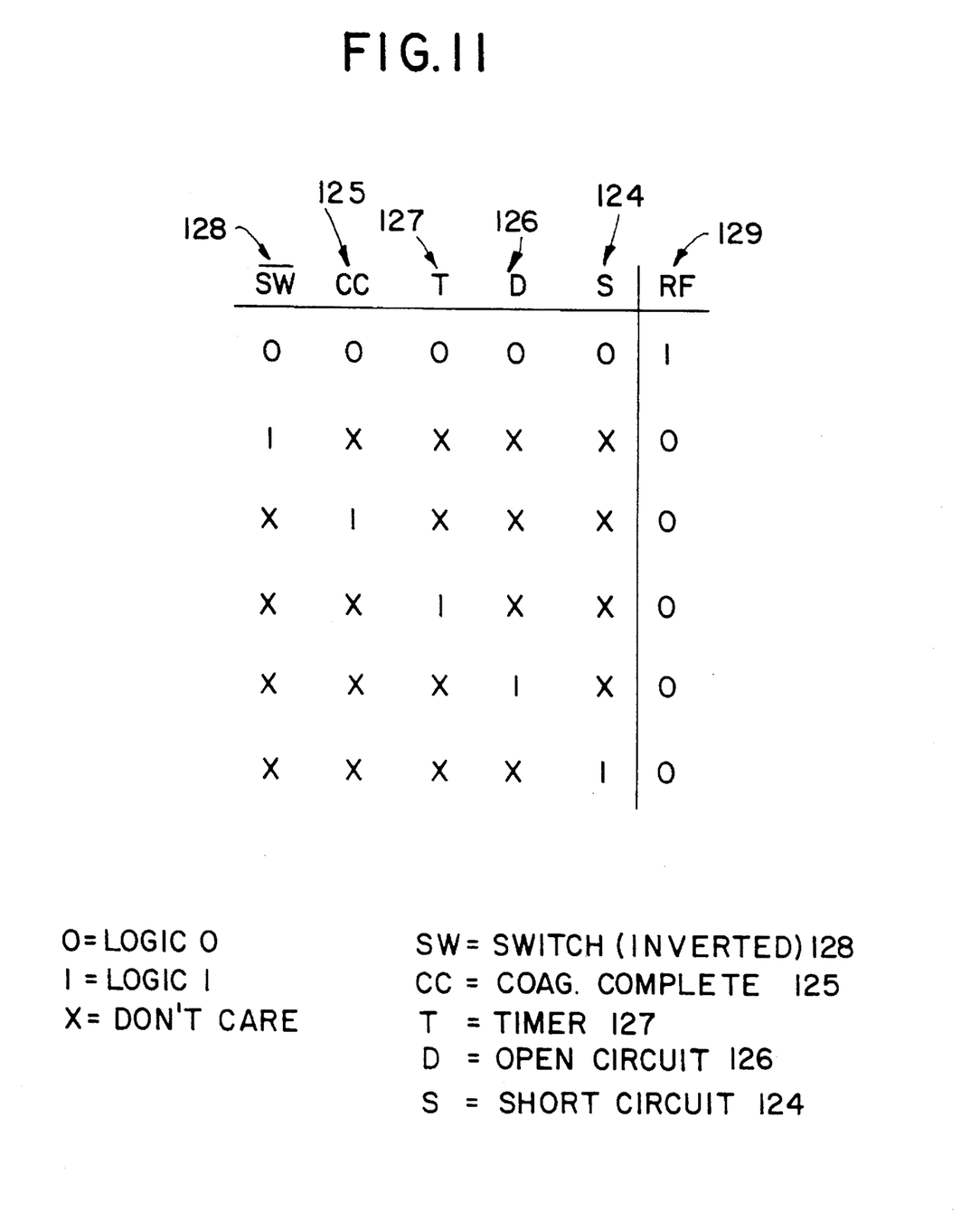
FIG. 11 is a logic diagram of the controller of FIG. 10 illustrating control logic for RF output control.

A signal is provided to a controller for each condition indicating whether or not a given condition exists. Upon the existence of one or more of these conditions the RF energy is automatically turned off by the controller. FIG. 11 illustrates the system logic of the controller 79. The controller 79 includes a short circuit input 124, a coagulation complete input 125, an open circuit input 126 and a time out input 127, as well as a reset input 128. The controller 79 also includes a RF control output 129 which switches on and/or off the RF generator delivery of electrosurgical energy to the tissue. As long as the output 129 is a logic 1, the RF is on. The output 129 is a logic 1 when coagulate complete 125, time out 127, short circuit 124, the open circuit 126 and the reset input 128, are all at a logic "0". If any one or more of the inputs 124, 125, 126, 127, 128 are at a logic "1" the RF control output 129 is a logic "0" and the RF is turned off.

A preferred embodiment provides a control device which controls the generator energy output based on load impedance. The load impedance is used to determine a preferred energy level, e.g., voltage, current or power level, based on a specific system load curve for a generator, instrument and/or application. The control device then compares the actual energy level for the measured impedance with the desired energy level and adjusts the generator output according to the difference between the two, i.e., preferably to minimize the difference between the two.

The specific load curve preferably reflects the voltage, current, power, for a range of impedance that will optimize performance of the instrument. The load curve may have various forms, for example, it may be continuous or may be stepped. The load curve may vary from generator to generator, for a particular instrument in use with the generator, or for a particular electrosurgical application of the generator. For example, in a one embodiment using an instrument such as described herein, three impedance ranges have been identified at which different energy requirements exist: Initially tissue impedance is in a lower range, e.g., approximately 20 to 100 ohms. In the lower ranges, more current is required to provide enough power to initiate tissue coagulation. A second, mid-range of impedances, e.g., approximately 100 to 500 ohms, requires enough power to maintain the coagulation process. A third range of higher impedances typically occurring towards completion of coagulation, e.g., approximately 500 ohms and above, requires the voltage be limited to prevent sparking and tissue sticking. Thus the system load curve in this embodiment would reflect both the inherent characteristics of the generator and voltage output at which optimum power is delivered for a particular impedance, as well as the specific power requirements for a predetermined instrument and application.

Referring to FIG. 10, a generator with a servo loop control device, is illustrated. The impedance signal 89 and the voltage $V_{RMS}$ signal 87 are fed back to the generator 70 through a control device which comprises a function fitting device 61 and an error amplifier 62. The control device causes the generator 70 to produce voltages within a desired range based on a load impedance fit to a specific load curve.

The impedance 89 is fed to a function fitting device 61. The output 64 of the function fitting device 61 represents a desired voltage based on the input impedance 89. This desired voltage function is the voltage required for the generator 70 to produce a particular, pre-determined load curve. Desired voltage output 64 along with actual voltage is fed into an error amplifier 62. The output 65 of the error amplifier 62 represents an error voltage which is fed into an analog multiplier 75 through a diode 77.

Alternatively, current, power or another energy parameter may be used to control the output of the energy source or generator 70. A signal corresponding to impedance of the target is input into the function fitting device which provides a desired current, power or other energy parameter output, which is then compared to the measured or calculated current, power or other energy parameter.

The diode 77 ensures first quadrant operation of the analog multiplier 75. The analog multiplier 75 functions as an amplitude modulator of oscillator 72 such that large error voltages at output 65 result in large outputs from RF amplifier 71. And small error voltages of output 65 result in smaller RF output from RF amplifier 71. Thus, generator 70 acts as a closed-loop servo system based on voltage such that a desired load curve is obtained. The loop compensation device 63 acts to stabilize the servo loop. If an electrical parameter other than voltage is used, the form fitting function preferably outputs a signal reflecting the difference in the alternative energy parameter.

Referring now to FIGS. 6–9 a flow chart illustrates a method for carrying out a microprocessor controlled embodiment of the present invention. When the system is turned on (block 200), the variables including $Z_{min}$, $V_{thresh}$, $I_{thresh}$, time over, and $Z_{initial}$, are initialized (block 201). The system continues to look for the activation of the RF switch (block 202). When the RF switch is turned on, the interrupts are set for RF Switch (block 203), for Short Circuit (block 204), and Open Circuit (block 205) so that when one of these interrupt conditions occur, the microprocessor automatically goes to the instructions associated with block 234.

After the interrupts are set, the timer is started (block 206). A sequence is run to check the RF amplifier health (block 207), e.g., to look for an Amplifier On signal or to check if certain voltages are in a suitable range. If the amplifier is operating properly, RF energy is turned on (blocks 208 and 209).

If the amplifier is not operating correctly, an RF Off request is made (blocks 209 and 210) and a Hardware Failure Alert flag is set (block 211). The system looks for a hardware failure flag (block 233). When the hardware failure is detected, the controller provides a hardware failure alert indication and shuts off. (blocks 243 and 244).

If hardware failure is not indicated (block 233), then $V_{rms}$ and $I_{rms}$ is read (block 235) to determine if any voltage or current is being supplied by the system (block 236). When the system is first initialized, until the instruction to turn on energy in block 209 is reached, there should be no current or voltage. If there is a voltage or current with the RF request off, then there is a hardware failure. A hardware failure alert is indicated and the program is stopped (blocks 243 and 244).

If RF energy is turned on (block 209), then the $V_{rms}$ and $I_{rms}$ are read and the impedance, Z, is calculated by dividing the $V_{rms}$ by the $I_{rms}$. (block 212). The controller checks to see if the $V_{enable}$ and $I_{enable}$ flags are set. (block 213). These flags are set when a minimum threshold voltage is present and a minimum threshold current is delivered through the electrodes of the device. (blocks 214, 215, 216, and 217).

If the $V_{enable}$ and $I_{enable}$ flags are set (213) the software looks for a time over condition to determine if the device has been on for a period of time in excess of a maximum. If a time over condition is recognized, the timer flag is set, RF energy is turned off (blocks 218 and 219) and a hardware failure check is run (block 233).

After looking for a time over condition, the controller checks for a short circuit or open circuit condition. If a short or open circuit exists, the corresponding short circuit or open circuit bit is set (block 220), RF energy is turned off (block 221), and a hardware failure check is run (block 233).

Figure 8:
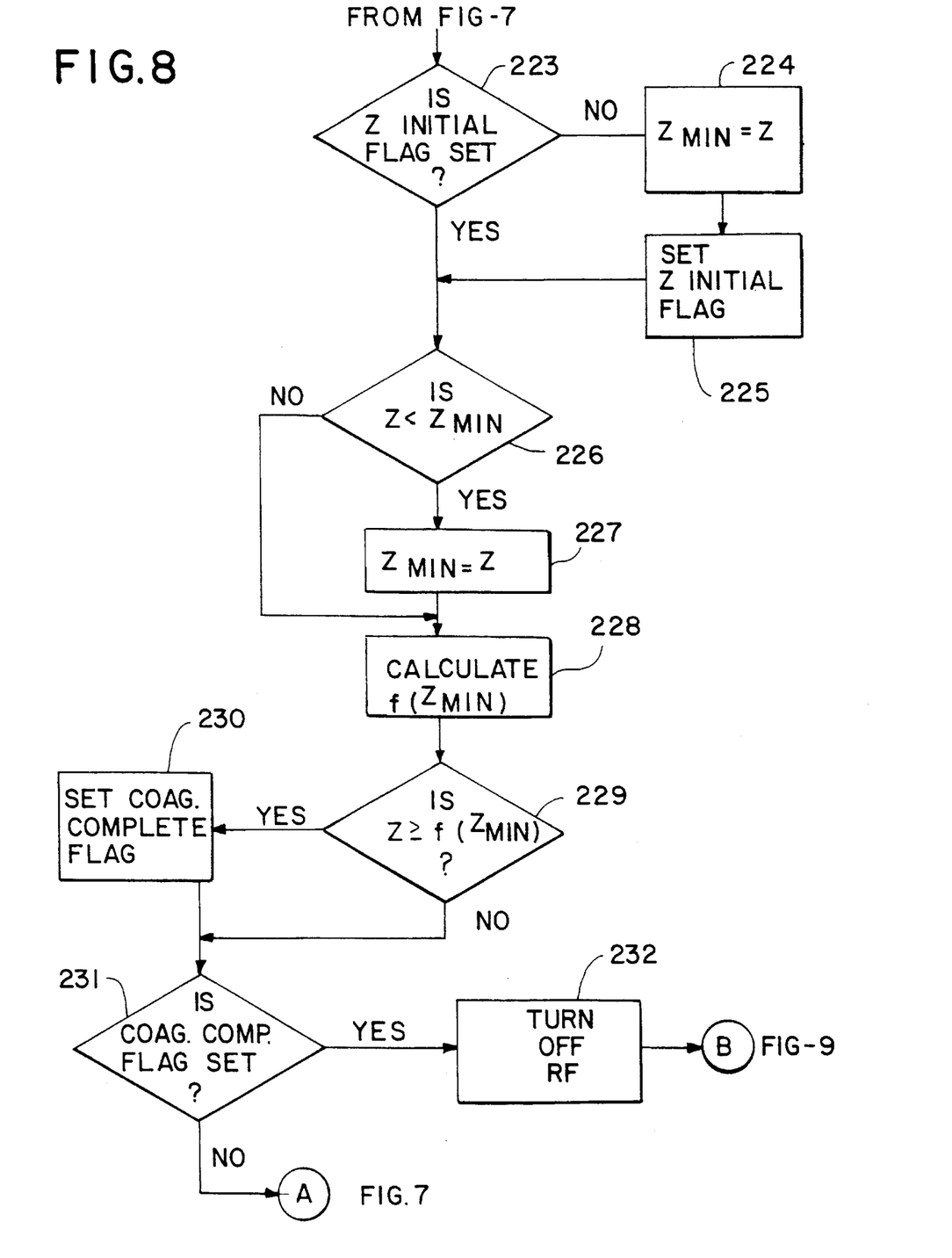
Figure 9:
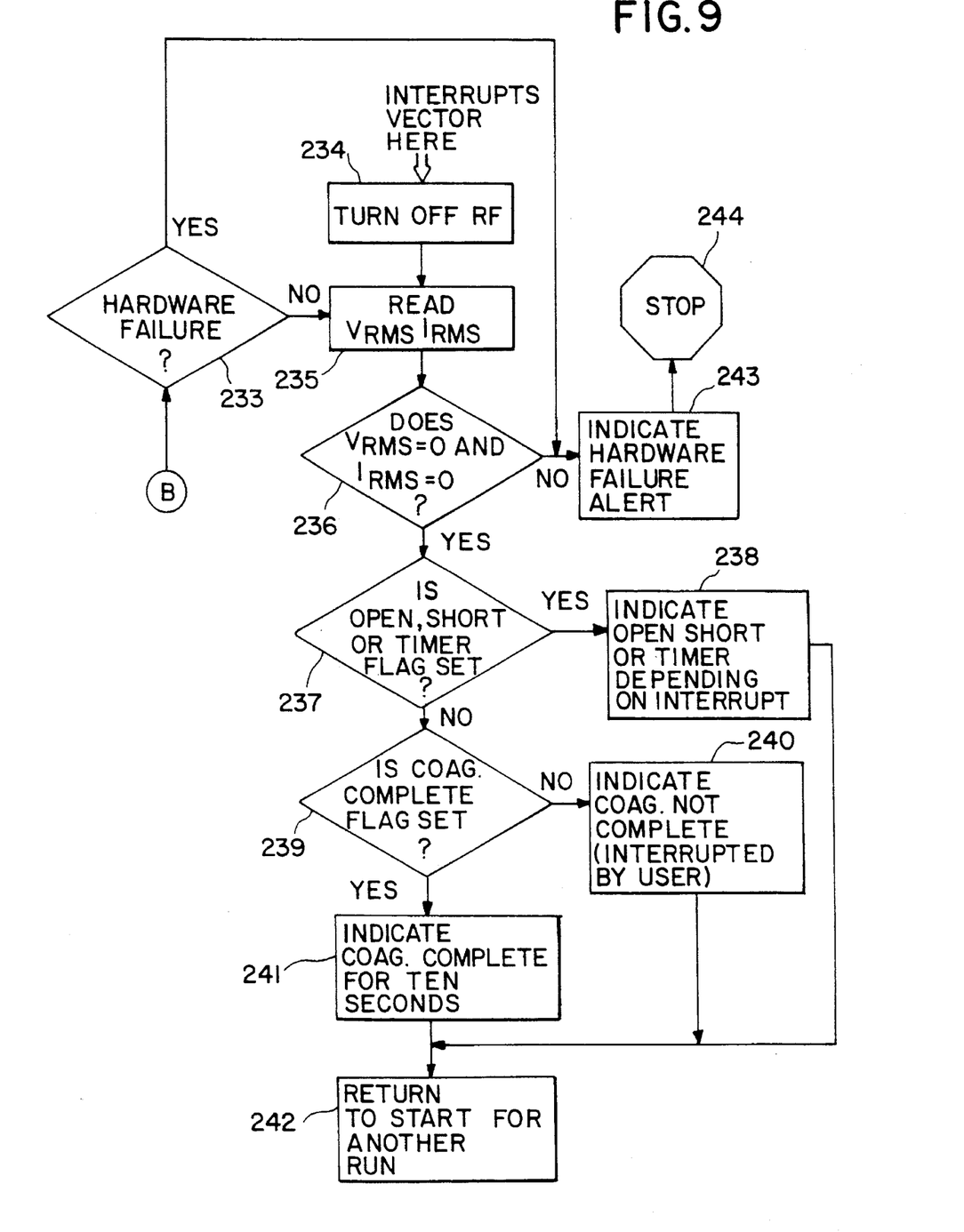

The controller checks again for $V_{enable}$ and $I_{enable}$ in block 222, before proceeding to the threshold determining portion of the circuit illustrated in FIG. 8. If the voltage or current did not exceed $V_{thresh}$ or $I_{thresh}$ in blocks 214 and 216, the controller iterates the sequence beginning at block 212 for detecting time over, short circuit, open circuit, i.e., the coagulation complete detection enable. This enables the device to wait until enough current and voltage is delivered to the circuit to check for the coagulation complete condition.

If the $V_{enable}$ and $I_{enable}$ flags are set, the short circuit and open circuit bits are not set (block 220), and the time over condition does not yet exist (block 219), the measured impedance used to determine if coagulation is complete as follows.

The Z initial flag is set during the first iteration and $Z_{min}$ is initially assigned the measured impedance value (blocks 223–225). Initially, $Z_{min}$ is the same as the measured impedance and thus block 227 is bypassed at block 226. A calculation is made of $f(Z_{min})$ (block 228). As long as the measured impedance is less than the $f(Z_{min})$, the sequence is iterated (229, 231). In the next iteration of blocks 223–231, the newly measured impedance is compared to the previous measured impedance which has been assigned $Z_{min}$ (block 226). As long as the impedance is decreasing, $Z_{min}$ will be reassigned the new value of the measured impedance (blocks 226 and 227) and the steps repeated. When the measured impedance is greater than or equal to $f(Z_{min})$, i.e. the threshold impedance, the coagulation complete flag is set (block 230). If coagulation complete flag is set, the RF is turned off (block 232) and the hardware failure check is run.

If after the initial run through the program a hardware failure alert occurs (block 233, 236) or an interrupt occurs, the program determines the cause and indicates as such (blocks 233–242). The $V_{rms}$ and $I_{rms}$ are read, (block 235). If no current or voltage is being delivered to the system, the controller checks to see if the open circuit, short circuit or time over flags have been set (block 237). If so then a signal indicates which flags have been set, and the program is returned to start (blocks 240, 242). Similarly, the controller checks for the coagulation complete flag (block 239). If there was the coagulation complete flag has been set, it will be indicated for ten seconds (block 241). If not, it will be indicated as not complete (block 240) and the program will return to point at the start (block 242). Preferably the electrical components selected to carry out the steps of FIGS. 6–9 are adapted to provide a complete iteration of all the steps at least every 1/50 second.

Referring now to FIGS. 1–5 there is illustrated an instrument to be used in conjunction with the impedance feedback device of the present invention. An endoscopic linear cutting and stapling instrument 10 is shown having a housing 16 coupled to a shaft 30 with a lumen extending therethrough and an end effector 15 extending from the distal end of the shaft 30. The end effector 15 comprises first and second elements which are comprised of interfacing jaw members 32, 34. Jaw member 32 is movably secured to jaw member 34. The housing 16 has a clamping trigger 12 for closing jaw members 32, 34. Jaw members 32, 34 are shown in an unclamped position in FIG. 2, in a clamped position prior to instrument firing in FIG. 3, and in a clamped position after instrument firing in FIG. 4.

Figure 1:
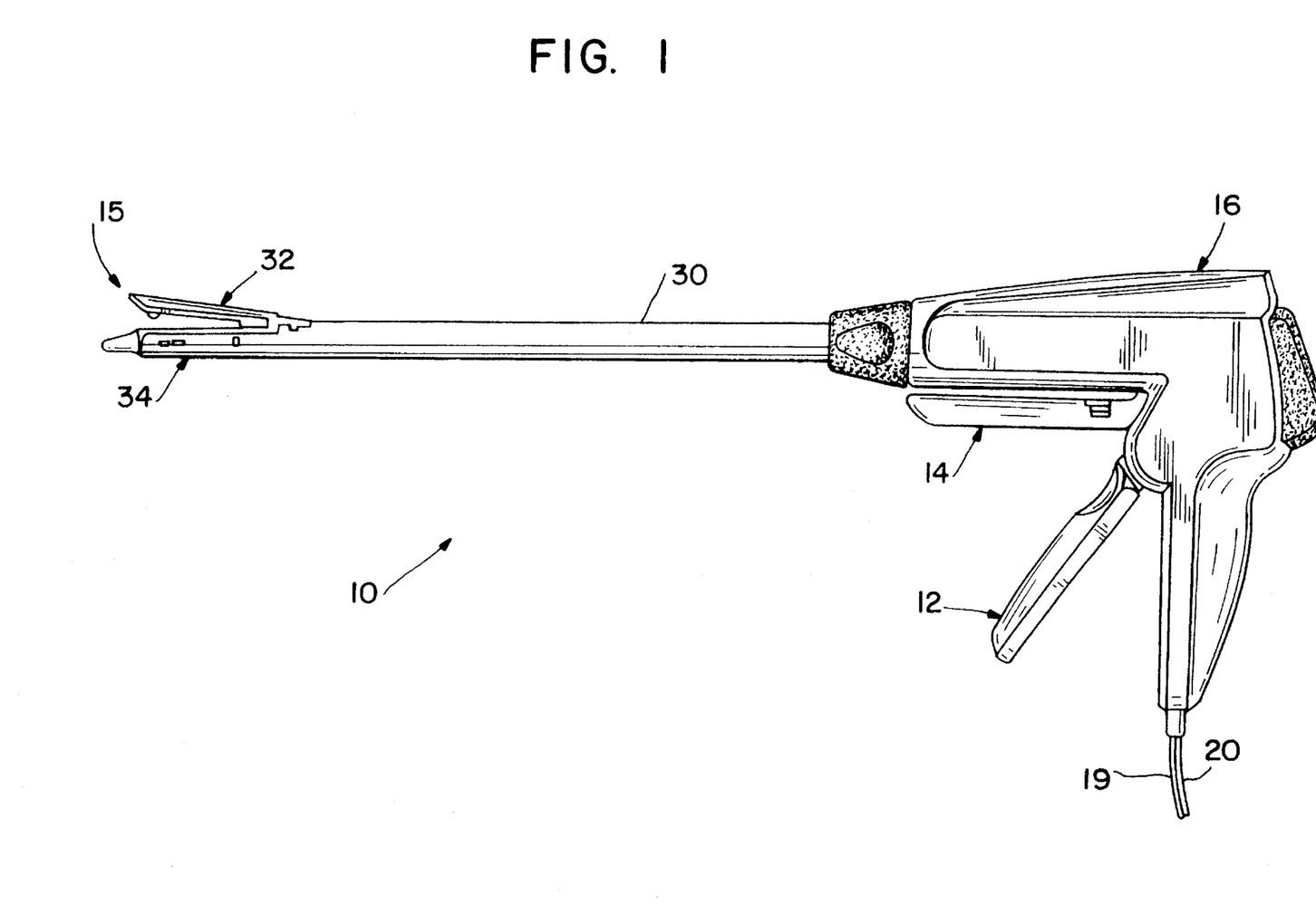
FIG. 1 is a side view of a bipolar endoscopic electrosurgical instrument operable in accordance with the present invention.
Figure 2:
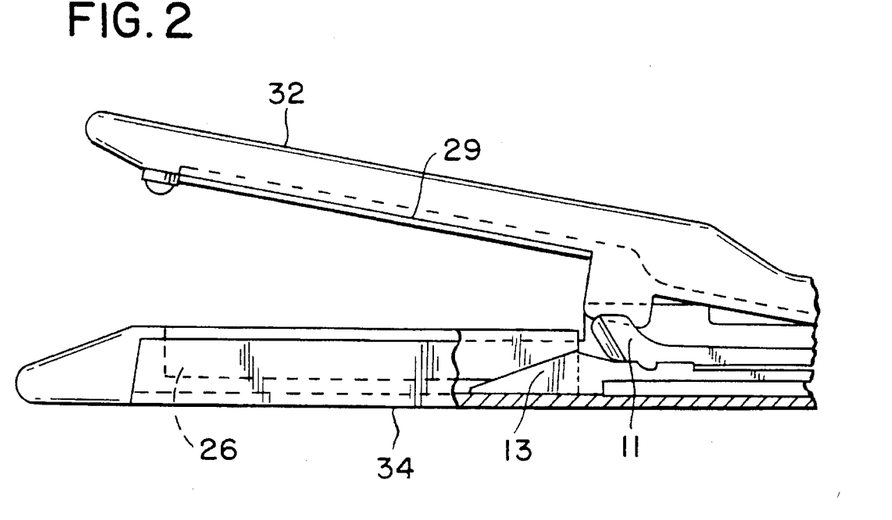
FIG. 2 is a partial cross-sectional view of the distal end of the instrument of FIG. 1 in an open position.
Figure 3:
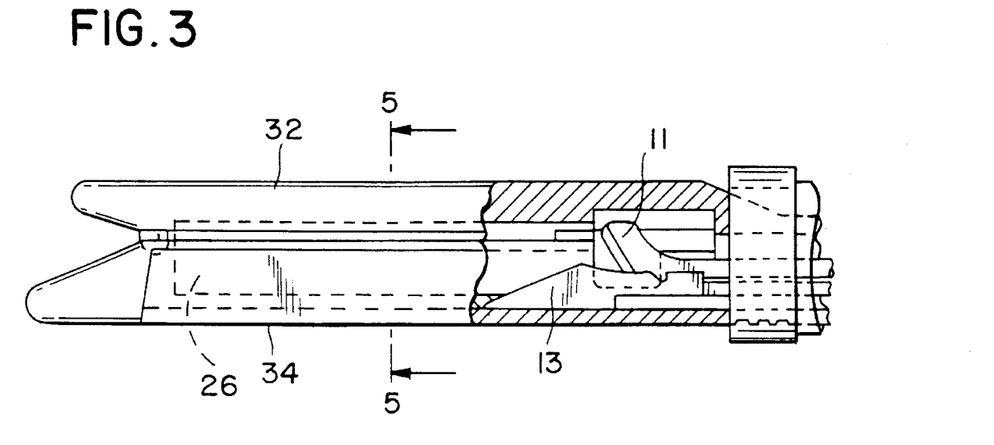
FIG. 3 is a partial cross-sectional view of the distal end of the instrument in FIG. 1 in a closed, unfired position.
Figure 4:
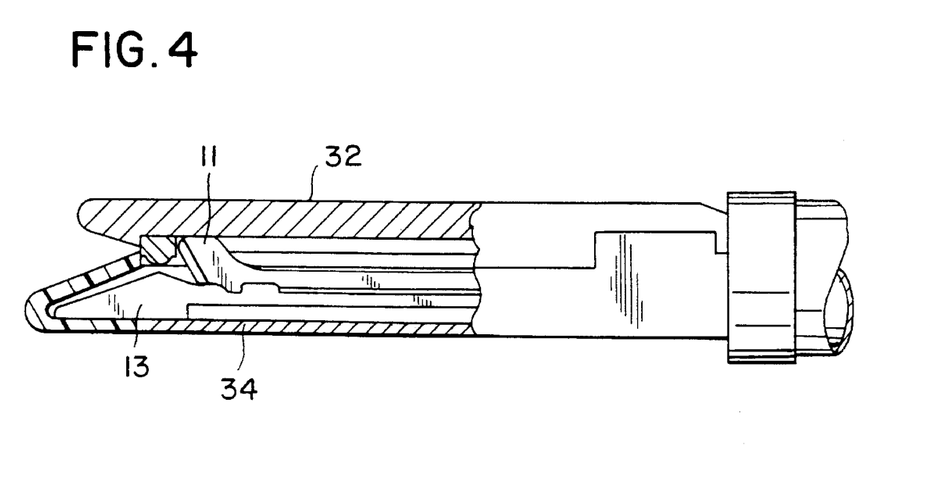
FIG. 4 is a partial cross sectional view of the distal end of the instrument in a closed, fired position.
Figure 5:
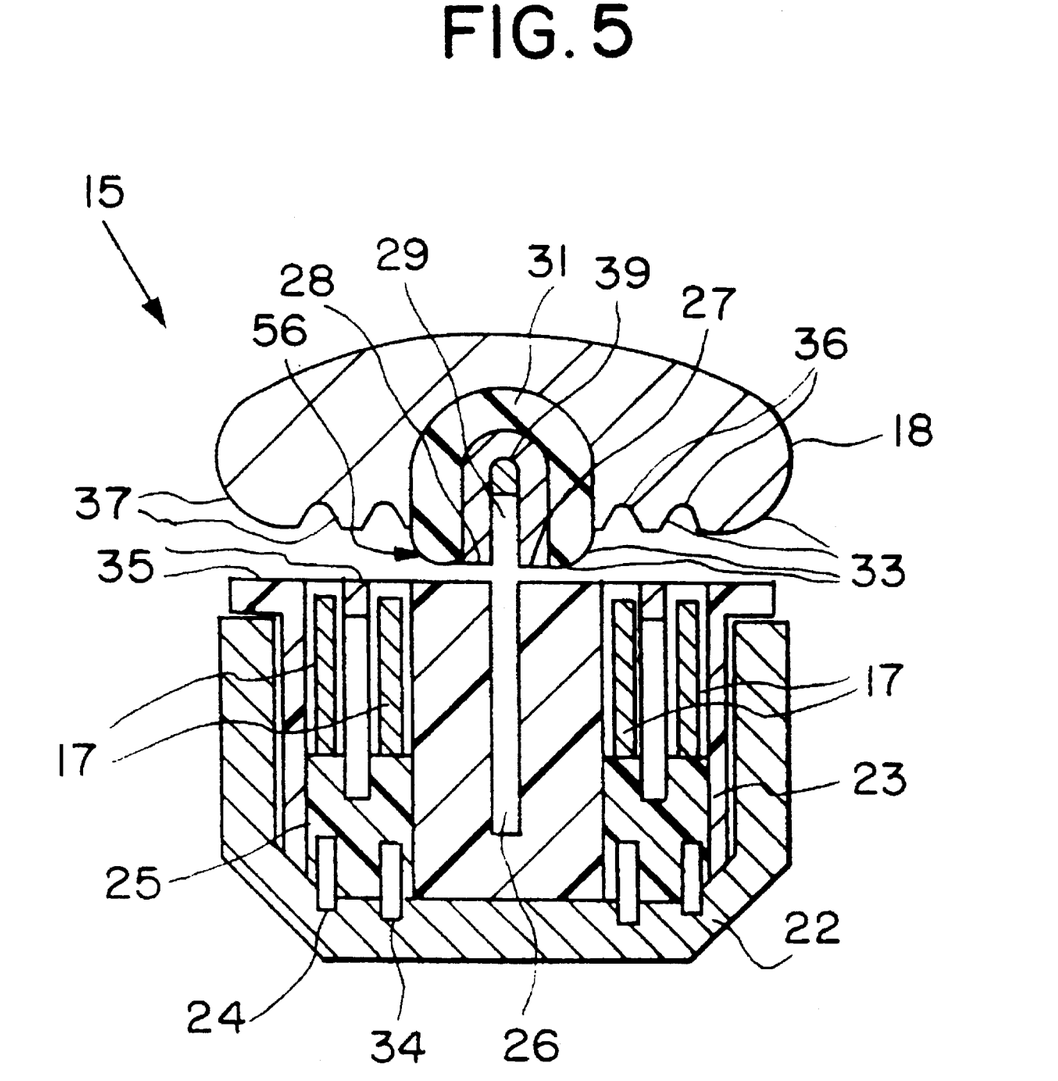
FIG. 5 is a front cross sectional view of the distal end of the instrument of FIG. 1 along the line 5—5.
Figure 6:
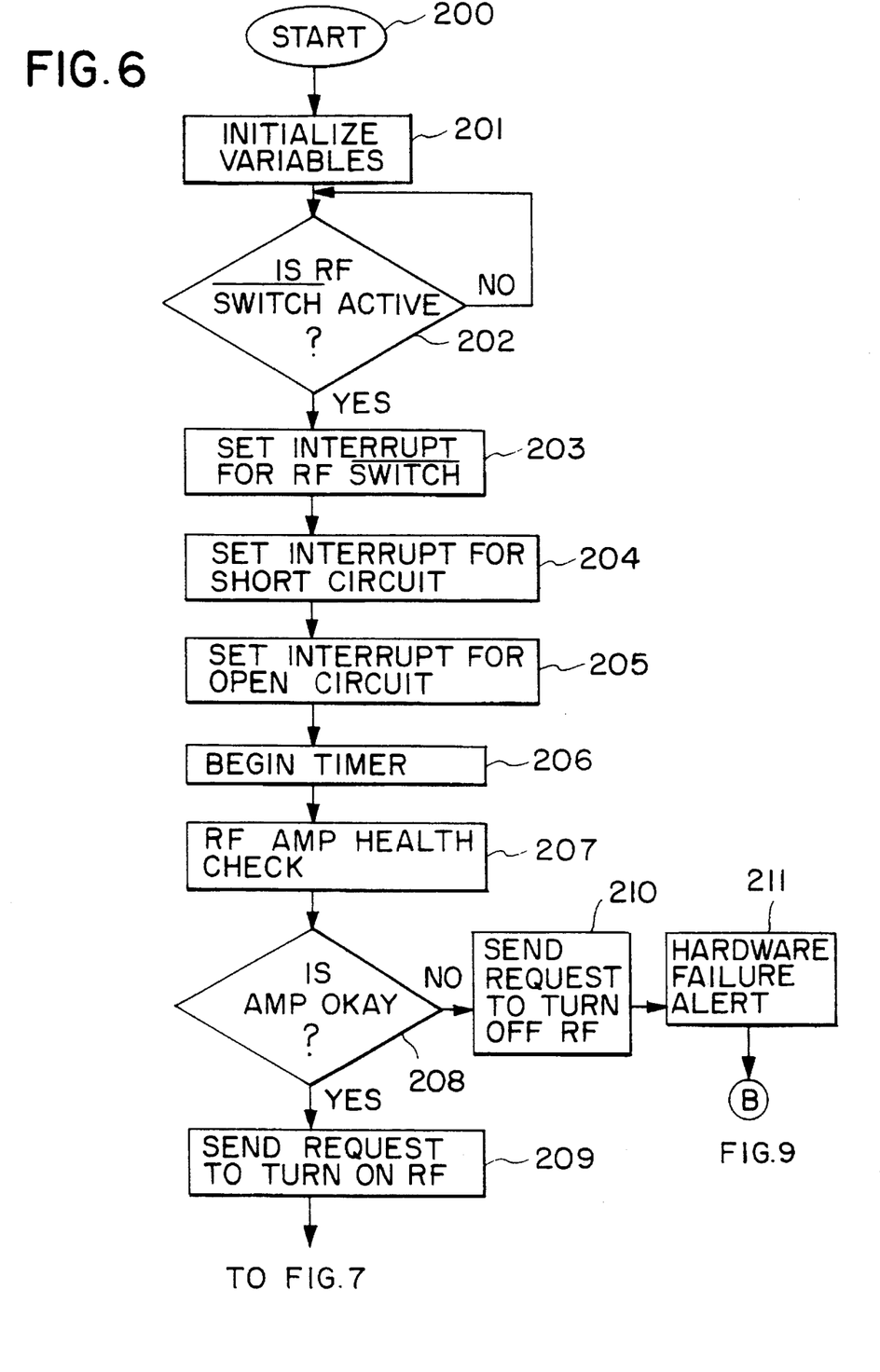
FIGS. 6–9 represent a schematic block diagram of a microprocessor controlled impedance monitoring apparatus for controlling the RF energy delivered by electrosurgical instrument of FIG. 1.
Figure 7:
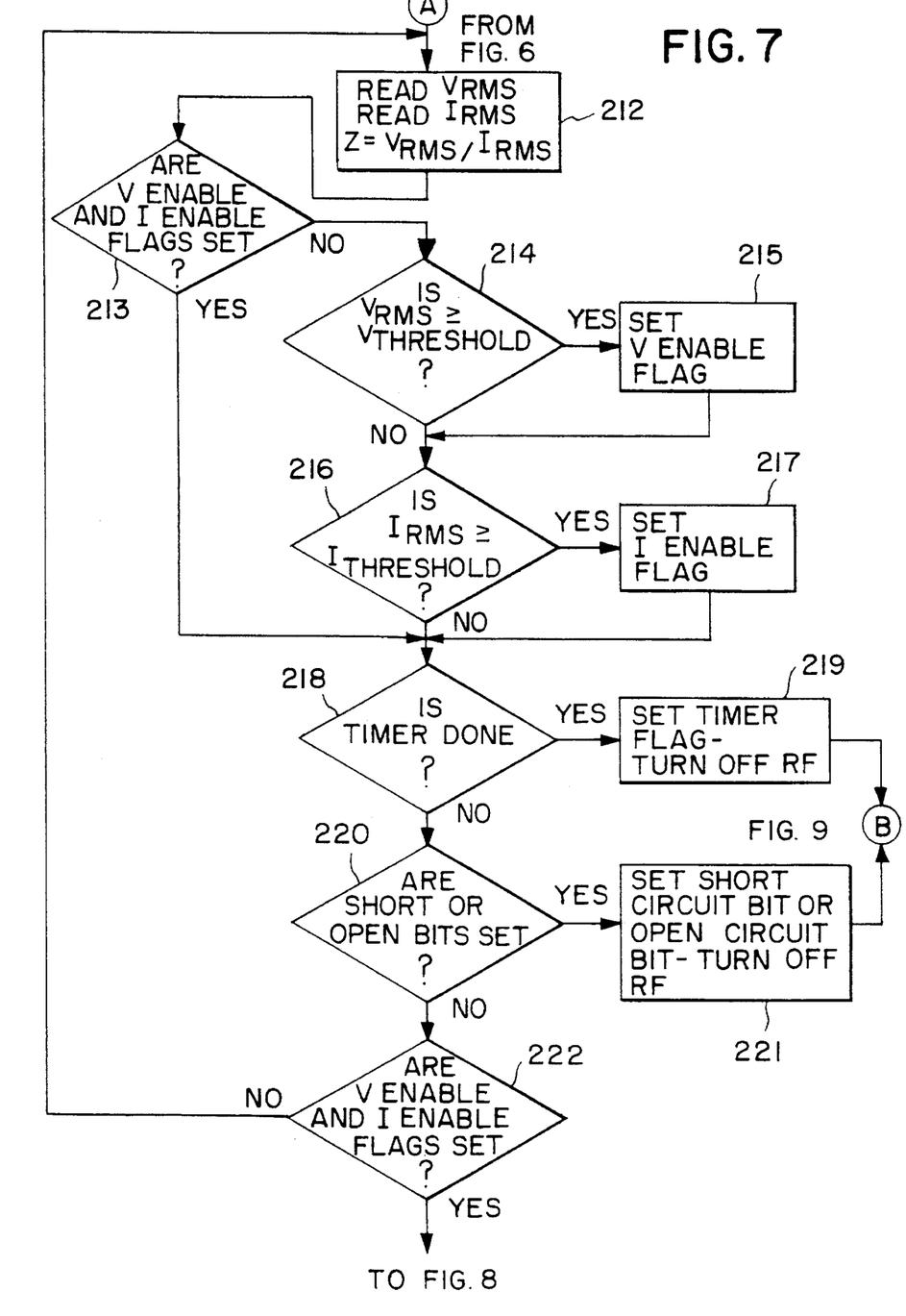

Jaw member 32 comprises an anvil 18, U-shaped electrode 39 extending along the length of the jaw 32, and a U-shaped insulating material 31 surrounding the outside of the electrode 39. Jaw member 32 has an inner surface 33 which faces an inner surface 35 of jaw member 34. The U-shaped electrode 39 comprises two electrically communicating electrode bars 27, 28 forming a first pole and located on and extending substantially along the length of the inner surface 33. The U-shaped electrode 39 is comprised of a conductor, such as, aluminum or surgical grade stainless steel. The bars 27, 28 are separated by a knife channel 29 extending longitudinally through the middle of the electrode 39. Pockets 36 located on anvil 18 for receiving staple ends are located along the inner surface 33, lateral to and outside of bars 27, 28. The electrode bars 27, 28 and insulating material 31 form a ridge 56 extending out relative to an anvil portion 37 of the inner surface 33 (FIG. 5). The electrode 39 acts as a first pole of a bipolar system. The anvil 18 is formed of an electrically conductive material and acts as a second pole of the bipolar system, electrically opposite to the first pole. The anvil 18 is electrically isolated from the electrodes by the U-shaped insulating material 31.

Bipolar energy may be supplied to the end effector 15 from electrosurgical generator 40 (FIG. 10) through wires 19, 20 extending into the body 16 of the instrument. The generator 40 is user controlled by way of switch 42 (FIG. 10). Wire 19 provides electrical current to the electrode 39 through electrical contact means extending through shaft 30. Wire 20 carries a current to the anvil 18 and is coupled to the anvil 18 through an electrical contact means extending through the shaft 30. The electrical circuit is closed when and only when the clamping trigger 12 is closed. A means of connecting the wire to the corresponding electrode as well as instrument actuation means are described in parent application Ser. No. 8/095,797, incorporated herein by reference.

Jaw member 34 comprises a cartridge channel 22 and a cartridge 23 inserted into the cartridge channel 22. The cartridge 23 includes a track 25 for wedge 13, a knife channel 26 extending longitudinally through the center of the cartridge 23, a series of drivers 24 extending into the track 25 and staples 17 arranged in two sets of parallel double rows. When tissue is engaged between clamped jaw members 32, 34, a firing trigger 14 located on housing 16 may be actuated to advance a cutting element 11 through the engaged tissue to cut the tissue. Simultaneously, when the firing trigger 14 is actuated, the wedge 13 is advanced through the track 25 causing the drivers to 24 to displace towards the staples 17, thereby driving the staples 17 through tissue and into anvil pockets 36.

In operation, the end effector 15 of the instrument is located at a tissue site where tissue is to be treated. The jaw members 32, 34 are opened and tissue is then placed between the interfacing inner surfaces 35, 33 respectively of jaw members 32, 34. The clamping trigger 12 is squeezed to cause the jaw members 32, 34 to close to locate and compress tissue between the interfacing inner surfaces 33, 35. The closure of the clamping trigger 12 also closes the electrical circuit. When the tissue has been appropriately situated between the jaw members 32, 34, a user may apply RF energy from the generator 40 using a user activated switch 42. Current flows through the compressed tissue between the electrode 39, i.e., the bars 27, 28, and the anvil 18.

After the RF energy is turned off, the controller indicates the instrument status, e.g., open circuit, short circuit, coagulation complete, time over. If the coagulation complete status is indicated, the firing trigger 14 may be actuated to advance cutting element 11 through knife channels 26, 29 to cut engaged tissue between the bars 27, 28 where the tissue has been cauterized. Simultaneously, the firing trigger 14 advances the wedge 13 through track 25 to advance drivers 24 to fire staples 17 through tissue and into pockets 36 of the anvil 18. Thus, the cut line is lateral to the coagulation lines formed by the bar electrodes 27, 28 and staples 17 are applied into longitudinally double rows on each side of the cutting element 11 as the cutting element 11 cuts the tissue.

The invention described and the specific details and the manner in which it may be carried out having been exemplified it will be readily apparent to those skilled in the art that innumerable variations, modifications, and extensions of the basic principles involved may be made without departing from the spirit and scope of the present invention. The impedance feedback system as described above is used to indicate when sufficient cauterization has occurred. When coagulation is complete, a signal may be provided by a controller to a user, or a controller may automatically turn off the RF energy. Other signals may be provided to an instrument user as well. For example a tone corresponding to the measured impedance may be provided to a user to audibly monitor the change in impedance.

It is also intended that this device and/or method be used with numerous types of electrosurgical instruments including monopolar, bipolar and multipolar configurations. The impedance feedback system may be included in part or in whole with the actual instrument, as a separate unit and/or with the energy source or generator.

What is claimed is:

1. An electrosurgical device for treating tissue during a surgical procedure, said device comprising:
    a surgical instrument having a tissue treating portion including an end effector adapted to engage tissue to be treated;
    electrically isolated first and second poles comprised of tissue contacting first and second electrodes adapted to receive electrosurgical energy from an energy source connected to said electrodes, said first and second electrodes being capable of conducting electrical energy therebetween, at least one of said first and second electrodes being connected to said tissue treating portion of said instrument;
    an energy control signal generated by an energy control signal generator for controlling RF energy supplied from said energy source to said electrodes;
    impedance measurement circuitry coupled to said electrodes for measuring the impedance of tissue engaged by said end effector, wherein said impedance measuring circuitry is adapted to determine a minimum impedance value, to determine a target impedance value as a function of said minimum impedance value and to compare measured impedance values to said target impedance value and alter said control signal when said measured impedance value exceeds said target impedance value.

2. The electrosurgical device of claim 1 further comprising:
    an energy source arranged to supply electrosurgical energy to said electrodes, wherein said energy source is responsive to said control signal to supply said energy to said electrodes.

3. The electrosurgical device of claim 1 wherein said impedance measuring circuitry includes:
    a first device for determining the minimum impedance value;
    a target determining device coupled to said first device, for determining the target impedance value as a function of said minimum impedance value; and
    a first comparison device for comparing measured impedance values to said target impedance value and generating a signal indicating whether said measured impedance value exceeds said target impedance value.

4. The electrosurgical device of claim 1 wherein said end effector includes first and second elements moveable relative to each other for engaging tissue therebetween, wherein said first electrode is located on at least one of said first and second elements.

5. The electrosurgical device of claim 4 wherein said second electrode is located on at least one of said first and second elements.

6. The electrosurgical device of claim 5 wherein said impedance measuring circuitry is adapted to measure the impedance of the tissue between said first and second electrodes and engaged by said first and second elements.

7. The electrosurgical device of claim 4, wherein:
    said first and second elements comprise first and second interfacing surfaces for engaging tissue to be electrosurgically treated;
    wherein said first pole is comprised of one or more first electrodes located on at least one of said first and second interfacing surfaces;
    wherein said second pole is comprised of one or more second electrodes located on at least one of said first and second interfacing surfaces; and
    wherein each of said one or more first electrodes is offset from each of said one or more second electrodes with respect to said interfacing surfaces.

8. The electrosurgical device of claim 1 wherein said impedance measurement circuitry comprises a microprocessor controller.

9. A method of operating a device for electrosurgically treating tissue during a surgical procedure, said method comprising the steps of:
    applying RF energy to tissue to be electrosurgically treated by means of an electrosurgical instrument;
    measuring the impedance of the tissue treated by said electrosurgical instrument;
    generating an impedance signal representative of the measured impedance value of said tissue;
    determining a representative minimum impedance value;
    determining a representative target impedance value as a function of said minimum impedance value;
    comparing measured impedance values to said target impedance value; and
    generating a control signal to control the RF energy to said electrosurgical instrument in response to said measured impedance value exceeding said target impedance value.

10. The method of claim 9 further comprising;

providing a tissue engaging instrument for engaging tissue to be electrosurgically treated, wherein said instrument includes electrically opposite tissue contacting electrodes;

engaging tissue to be electrosurgically treated between said electrodes; and applying electrical energy to tissue engaged between said electrodes.

11. An electrosurgical impedance feedback control device, said device comprising:

impedance measurement circuitry adapted to be coupled to tissue contacting electrodes connected to a tissue treating portion of a surgical instrument and to an energy source arranged to supply therapeutic electrosurgical energy to said electrodes, wherein said impedance measurement circuitry is adapted to measure the impedance of tissue engaged by the tissue treating portion of the surgical instrument;

said impedance measuring circuitry comprising:

a first device for determining a minimum impedance value;

a target determining device coupled to said first device, for determining the target impedance value as a function of said minimum impedance value; and a first comparison device for comparing measured impedance values to said target impedance value and generating a signal indicating whether said measured impedance value exceeds said target impedance value.

* * * * *